US00PP36297P2

(12) United States Plant Patent
Bennett

(10) Patent No.: US PP36,297 P2
(45) Date of Patent: Dec. 10, 2024

(54) ROSE HYBRIDA SHRUB NAMED "AUSCP17431"

(50) Latin Name: *Rosa hybrida*
Varietal Denomination: AUSCP17431

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 18/445,726

(22) Filed: Jan. 2, 2024

(51) Int. Cl.
*A01H 5/02* (2018.01)
*A01H 6/74* (2018.01)

(52) U.S. Cl.
USPC ..... Plt./439

(58) Field of Classification Search
USPC ..... Plt./107, 102
See application file for complete search history.

(56) References Cited

U.S. PATENT DOCUMENTS

PP17,267 P2 * 12/2006 Austin ..... A01H 6/749 Plt./107

OTHER PUBLICATIONS https://www.helpmefind.com/rose/l.php?l=2.91319.1 (Retrieved on Jun. 21, 2024) (Year: 2023).*
CPVO Application Consultation for 'AUSCP17431'. https://online.plantvarieties.eu/publicConsultationDetails?registerId=20240389&denomination=auscp17431. 2 pages. (Year: 2024).*

* cited by examiner

*Primary Examiner* — Karen M Redden
*Assistant Examiner* — Zachariah Allan Kay
(74) *Attorney, Agent, or Firm* — KPPB LLP

(57) ABSTRACT

A variety of rose plant of the shrub class, named 'AUSCP17431'. The 'AUSCP17431' is a variety of a cut rose bearing large blooms with a mid-pink color and a strong fragrance.

1 Drawing Sheet

Classification: The present invention relates to a new *Rosa hybrida* shrub of the market class 'English Rose'.

Variety denomination: The new plant has the varietal denomination 'AUSCP17431'.

ORIGIN OF INVENTION

This invention relates to a new and distinct variety of shrub rose plant named 'AUSCP17431', which was originated from the cross-pollination of the two 'unnamed' and unpatented seedlings of *Rosa hybrida.*

BACKGROUND OF THE INVENTION

The primary objective of this breeding was to produce a cut rose variety bearing large blooms with many petals, a mid-pink color and a strong fragrance.

SUMMARY OF THE INVENTION

Among the features which distinguish the new variety from others presently available and commercial rose cultivars known to the inventor is the following combination of characteristics: mid-pink colored blooms that are many petalled with large double blooms, strong stems, a strong fragrance and growth habit suitable for cut rose production.

Asexual reproduction of the new variety by cutting taken from stems as performed in Albrighton, United Kingdom shows that the foregoing and other distinguishing characteristics come true to form and are established and transmitted through succeeding asexual propagations. 'AUSCP17431' may be asexually propagated by cuttings taken from stems.

COMPARISON WITH PARENTS

The maternal and paternal parents of 'AUSCP17431' are two unnamed seedlings. The new rose may be distinguished from its seed parent, by the following combination of characteristics: the seed parent has a flower which is yellow in color, with a high number of prickles, whereas 'AUSCP17431' is a mid-pink color and has less prickles. The new rose may be distinguished from its pollen parent, by the following combination of characteristics: the pollen parent is yellow in color with much more lax growth which is not suitable for cut rose production, whereas 'AUSCP17431' is a mid-pink color with more upright, straight stems which are suitable for cut rose production.

COMPARISON WITH THE CLOSEST COMMERCIALLY AVAILABLE CULTIVAR

The most similar rose variety is 'AUSIMMON' (U.S. Plant Pat. No. 17,276). 'AUSIMMON' exhibits a smaller bloom diameter when compared to 'AUSCP17431'. 'AUSIMMON' also exhibits a medium to strong fragrance as compared to the stronger fragrance of 'AUSCP17431'. The petal count between the two roses is also different, with 'AUSIMMON' having approximately 120 petals per bloom, and 'AUSCP17431' has approximately 140 petals per bloom.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of cut 'AUSCP17431' specimens were made in a greenhouse in Albrighton, Wolverhampton, United Kingdom. The following description is of 8-year-old rose plants of the new variety grown in a greenhouse environment in Albrighton, United Kingdom in the month of May. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.2 cm long and 1.75 cm in diameter when the petals start to unfurl.

*Form*.—The bud form is long pointed ovoid.

*Color*.—When sepals first divide, the bud color is RHS 60A (red-purple group). When half blown, the upper sides of the petals are RHS 55A (red group), and the lower sides of the petals are RHS 55B (red group).

*Calyx*.—Shape: opens as a star shape and folds back against the stem. Length: 7 cm. Diameter: 7 cm.

*Sepals*.—Arrangement: Regular. Color: Upper Surface: RHS 147C (yellow-green group). Lower Surface: RHS 143A (green group). Length: 2.9 cm. Width: 1.1 cm. Shape: Lanceolate. Apex: Lanceolate. Margin: Smooth, slightly hairy. Surface texture: Upper Surface: Smooth, hairy. Lower Surface: Smooth. Number: There are 3 lightly appendaged sepals, and 2 unappendaged sepals with hairy edges.

*Receptacles*.—Color: RHS 144B (yellow-green group). Shape: Pitcher shaped. Size: Medium, about 1 cm long×1.2 cm wide. Surface: Smooth.

*Peduncle*.—Length: Medium, averaging about 6.3 cm. Surface: Rough, prickly. Color: RHS 144A (yellow-green group) Strength: Normal.

Blooms:

*Size*.—Large, average open diameter is about 11 cm and average depth is about 4 cm.

*Borne*.—Singly with the other blooms being nipped out for single bloom cut rose production.

*Peduncle*.—Strength: Normal Length: Averaging about 6.3 cm. Diameter: 0.4 cm.

*Form*.—When first open, bloom is cupped. Permanence of bloom: Flattens, outer petal edges curl slightly.

*Petalage*.—Number of petals under normal conditions: Approximately 140.

*Color*.—The upper sides of the petals are RHS 55B (red group). The reverse sides of the petals are between RHS 55B (red group) and RHC 55C (red group). The base of the petals has a medium to large basal spot that is RHS 12A (yellow group) in color.

*Variegations*.—None.

*Discoloration*.—The general tonality at the end of the first day is RHS 50A (red group), and at the end of the third day is RHS 55A (red group).

*Fragrance*.—Strong. Character of fragrance: Fruity, Old Rose.

Petals:

*Texture*.—Smooth and thick.

*Size*.—Width: 4.3 cm. Length: 4.9 cm.

*Surface*.—Smooth.

*Shape*.—Round, Pointed (outer petals); Obovate (inner petals).

*Margin*.—Entire.

*Apex shape*.—Rounded.

*Base shape*.—Accuminate.

*Form*.—Flat.

*Arrangement*.—Informal.

*Petaloids*.—Number: Between 0-5. Color: RHS 55A (red group). Length: 0.8 cm. Width: 0.6 cm. Shape: Obovate. Margin: Irregular.

*Persistence*.—Petals drop off cleanly before drying.

*Lastingness*.—On the plant: Not tested. As a cut flower: Long, about 10 days.

Reproductive parts:

*Stamens*.—Number: 10-15 per bloom. Length: Approximately 0.6 cm.

*Anthers*.—Length: 0.3 cm. Color: RHS 5B (yellow group). Arrangement: Regular around styles.

*Filaments*.—Color: RHS 5B (yellow group). Length: 0.3 cm.

*Pollen*.—Color: RHS 5B (yellow group).

*Pistils*.—Number: Between 120-150 per bloom. Length: approximately 0.8 cm.

*Styles*.—Color: RHS 196D (greyed-green group) Length: 0.6 cm.

*Stigmas*.—Color: RHS 5C (yellow group). Length: approximately 0.1 cm.

*Hips*.—None observed.

PLANT CHARACTERISTICS

Plant form: Shrub.

Plant growth: Vigorous.

Age to maturity: 2 years.

Mature plant: Height: 120 cm. Width: 80 cm.

Rootstock: Own root (production from cuttings) for the roses observed in the United Kingdom.

Foliage:

*Number*.—Leaflets on normal mid-stem leaves is: 5 (including terminal leaflet).

*Size*.—Very large, about 20.5 cm long×16.4 cm wide.

*Quantity*.—Sparse. Number of leaves per flowering stem is: 3-5.

*Color*.—New foliage: Upper side: RHS 185A (grey-purple group) with venation RHS 143B (green group). Lower side: RHS 199B (grey-brown group) with a tinge of RHS 144B (green group) on venation. Old foliage: Upper side: RHS 137A (green group). Lower side: RHS 146A (yellow-green group).

Leaflets:

*Size*.—About 8.3 cm long×5.6 cm wide.

*Shape*.—Pointed oval.

*Base shape*.—Cordate.

*Apex shape*.—Accuminate.
*Texture*.—Upper side: Leathery. Lower side: Leathery.
*Edge*.—Serrated.
*Serrations*.—Single, large.
*Petiole*.—Color: Center is RHS 145C (yellow-green group), perimeter is RHS 143A (green group). Length: 4.3 cm. Width: 0.15 cm. Upper Surface Texture: Smooth.
*Petiole rachis*.—Color: Center is RHS 145C (yellow-green group), perimeter is RHS 143A (green group). Length: 5 cm. Diameter: 0.2 cm. Underside: Smooth with prickles. Lower surface texture: Smooth.
*Stipules*.—Length: 1.5 cm. Shape: Lateral. Descriptor: Smooth. Apex: Acute. Color: RHS 143A (green group).
*Auricle*.—Shape: Lanceolate. Length: 0.5 cm. Width: 0.1 cm. Color: RHS 143A (green group).
*Vein color*.—Central vein RHS 151A (yellow-green group), rest of venation RHS 147A (yellow-green group).
*Venation pattern*.—Reticulate.

Wood:
*New wood*.—Color: RHS 146D (yellow-green group). Bark: Smooth.
*Old wood*.—Color: RHS 146C (yellow-green group) with streaks of RHS 186A (grey-purple group). Bark: Smooth.

Branching habit:
*Number*.—Not applicable.
*Dimensions*.—Not applicable.

Stems:
*Mature stem*.—Length.—90 cm. Diameter: 0.6 cm.
*Internode distance*.—10 cm. The above measurements are all variable, depending on growing conditions in a season.
*Stem pubescence present*.—No.

Prickles:
Large prickles:
*Quantity*.—On main canes from base: Few. Number per stem length: 2-4 per 30 cm.
*Form*.—Hooked downward, deep concave.
*Length*.—0.6 cm.
*Color when young*.—RHS 59B (red-purple group).
*Color when mature*.—RHS 59B (red-purple group).

Small prickles:
*Quantity*.—Main stalk: Many. Number per stem length: 25 per 30 cm.
*Color when young*.—RHS 59B (red-purple group).
*Color when mature*.—RHS 59B (red-purple group).

Disease resistance:
*Powdery mildew* (*podosphaera pannosa*).—Resistant.
*Downy mildew* (*peronospora species*).—Resistant.
*Blackspot* (*diplocarpon rosae*).—Resistant.
*Rust* (*phragmidium tuberculatum*).—Resistant.

Pest resistance: Not tested.
Winter hardiness: Not tested.
Growing conditions: Normal greenhouse conditions for cut rose production.

What is claimed is:

1. A new and distinct variety of rose plant of the shrub class named 'AUSCP17431', substantially as herein shown and described herein.

* * * * *

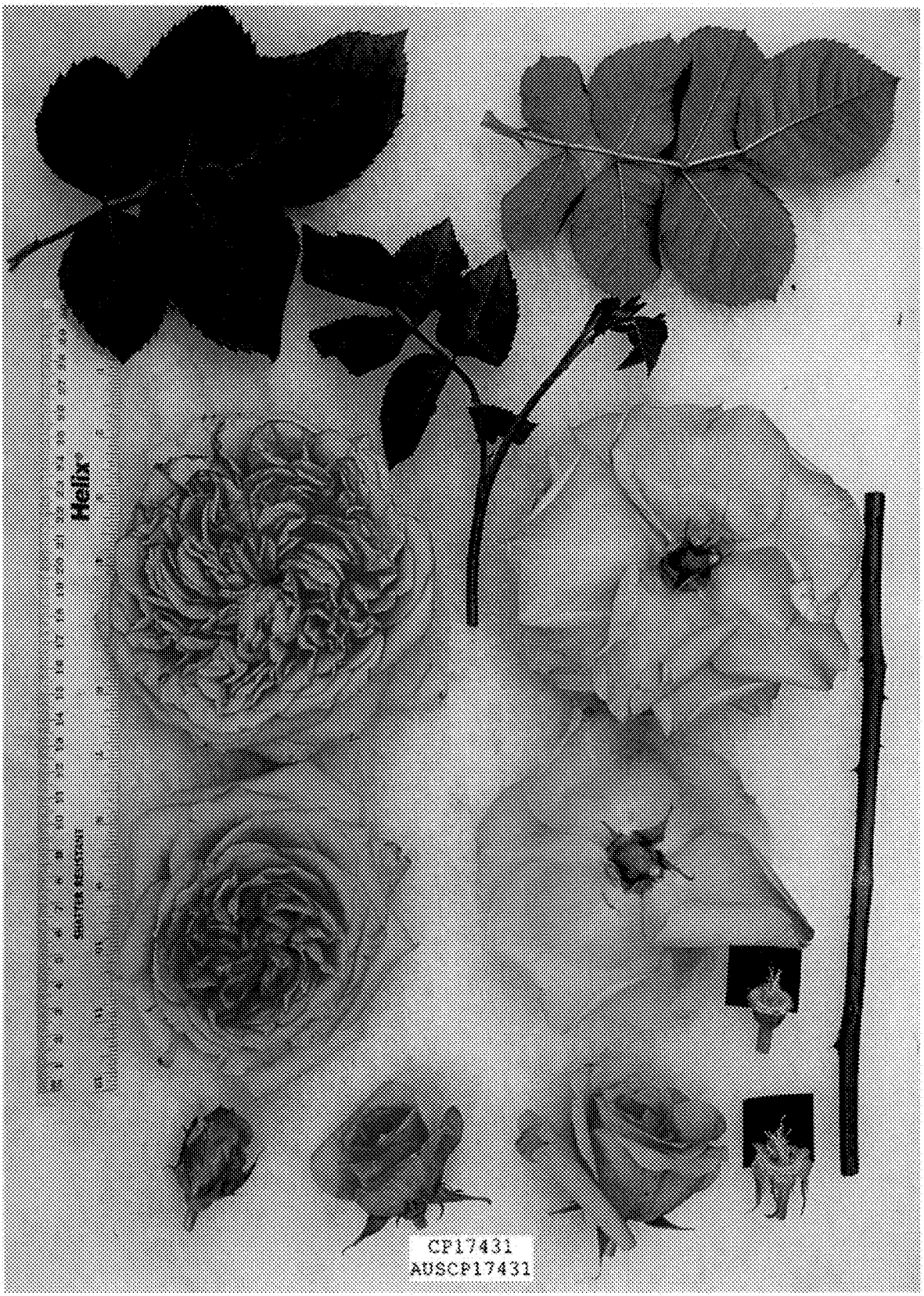
Helix
SHUTTER RESISTANT
CP17431
AUSCP17431